United States Patent
Riley et al.

(10) Patent No.: US 11,205,113 B2
(45) Date of Patent: *Dec. 21, 2021

(54) NEURAL NETWORK FOR PROCESSING GRAPH DATA

(71) Applicant: Google LLC, Mountain View, CA (US)

(72) Inventors: Patrick F. Riley, Los Altos, CA (US); Marc Berndl, Mountain View, CA (US)

(73) Assignee: Google LLC, Mountain View, CA (US)

(*) Notice: Subject to any disclaimer, the term of this patent is extended or adjusted under 35 U.S.C. 154(b) by 21 days.

This patent is subject to a terminal disclaimer.

(21) Appl. No.: 16/525,008

(22) Filed: Jul. 29, 2019

(65) Prior Publication Data

US 2019/0354840 A1 Nov. 21, 2019

Related U.S. Application Data

(63) Continuation of application No. 14/842,774, filed on Sep. 1, 2015, now Pat. No. 10,366,324.

(51) Int. Cl.
*G06N 3/04* (2006.01)
*G16C 20/70* (2019.01)

(52) U.S. Cl.
CPC ........... *G06N 3/0454* (2013.01); *G16C 20/70* (2019.02)

(58) Field of Classification Search
CPC .............................. G06N 3/0454; G16C 20/70
See application file for complete search history.

(56) References Cited

U.S. PATENT DOCUMENTS

| 2010/0205124 A1* | 8/2010 | Ben-Hur ................ G06N 20/00 706/12 |
| 2014/0279774 A1 | 9/2014 | Wang et al. |
| 2015/0220833 A1 | 8/2015 | Le Quoc |

FOREIGN PATENT DOCUMENTS

WO  WO 1999/35599  7/1999

OTHER PUBLICATIONS

Agatonovic-Kustrin, et al., "Basic concepts of artificial neural network (ANN) modeling and its application in pharmaceutical research", Journal of Pharmaceutical and Biomedical Analysis, 22(2000)717-727 (Year: 2000).*

(Continued)

Primary Examiner — Tsu-Chang Lee
(74) Attorney, Agent, or Firm — Fish & Richardson P.C.

(57) ABSTRACT

Methods, systems, and apparatus, including computer programs encoded on computer storage media, for receiving graph data representing an input graph comprising a plurality of vertices connected by edges; generating, from the graph data, vertex input data representing characteristics of each vertex in the input graph and pair input data representing characteristics of pairs of vertices in the input graph; and generating order-invariant features of the input graph using a neural network, wherein the neural network comprises: a first subnetwork configured to generate a first alternative representation of the vertex input data and a first alternative representation of the pair input data from the vertex input data and the pair input data; and a combining layer configured to receive an input alternative representation and to process the input alternative representation to generate the order-invariant features.

20 Claims, 8 Drawing Sheets

(56) References Cited

OTHER PUBLICATIONS

Azam, Farooq. "Biologically inspired modular neural networks." PhD diss., Virginia Tech, 2000.
Bonchev, Danail Chemical graph theory: introduction and fundamentals. vol. 1. CRC Press, 1991.
Bruna et al., "Spectral Networks and Locally Connected Networks on Graphs," http://arxiv.org/abs/1312.6203, May 21, 2014, 14 pages.
Ceroni et al. "Classification of small molecules by two- and three-dimensional decomposition kernels," Bioinformatics, vol. 23(16) Jun. 5, 2007, 8 pages.
Goodfellow et al., "Maxout networks," arXiv, Sep. 2013, 9 pages.
Henaff et al., "Deep Convolutional Networks on Graph-Structured Data," http://arxiv.org/abs/1506.05163, Jun. 16, 2015, 10 pages.
Hosoya, Haruo. "Topological index. A newly proposed quantity characterizing the topological nature of structural isomers of saturated hydrocarbons." Bulletin of the Chemical Society of Japan 44, No. 9 (1971): 2332-2339.
International Preliminary Report on Patentability issued in International Application No. PCT/US2016/046759, dated Mar. 15, 2018, 8 pages.
International Search Report and Written Opinion issued in International Application No. PCT/US2016/046759, dated Mar. 9, 2017, 12 pages.
Jothi et al. "Hybrid neural network for classification of graph structured data," International Journal of Machine Learning and Cybernetics, vol. 6(3) Jan. 28, 2014, 10 pages.
Kearnes et al. "Molecular Graph Convolutions: Moving Beyond Fingerprints," arXiv 1603.00856 Mar. 2, 2016, 22 pages.
Knisley et al. "Predicting protein-protein interactions using graph invariants and a neural network," Computation Biology and Chemistry, col. 35(2) Apr. 1, 2011, 6 pages.
Lecun et al. "Deep Learning," Nature, vol. 521(7553) May 27, 2015, 9 pages.
Maxwell, Sean, Mark R. Chance, and Mehmet Koyuturk. "Efficiently enumerating all connected induced subgraphs of a large molecular network." In International Conference on Algorithms for Computational Biology, pp. 171-182. Springer, Cham, 2014.
Merkwirth et al. "Automatic Generation of Complementary Descriptors with Molecular Graph Networks," Journal of Chemical Information and Modeling, vol. 45(5), Sep. 1, 2005, 10 pages.
Rogers et al. "Extended-connectivity Fingerprints," Journal of Chemical Information and Modeling, vol. 50(5) May 24, 2010, 13 pages.
Sperduti et al. "Supervised Neural Networks for the Classification of Structures," IEEE Transactions on Neural Networks, vol. 8, No. 3, May 1997 (Year: 1997).
Todeschini, Roberto, and Viviana Consonni Handbook of molecular descriptors. vol. 11. John Wiley & Sons, 2008.
CN Office Action in Chinese Application No. 201680034801.7, dated Feb. 20, 2021, 26 pages (with English translation).
EP Office Action in European Application No. 16754627.4, dated Mar. 4, 2021, 6 pages.

\* cited by examiner

NEURAL NETWORK FOR PROCESSING GRAPH DATA

CROSS-REFERENCE TO RELATED APPLICATION

This is a continuation of U.S. application Ser. No. 14/842,774, filed on Sep. 1, 2015, the disclosure of which is considered part of and is incorporated by reference in the disclosure of this application.

BACKGROUND

This specification relates to a neural network for processing graph data.

Neural networks are machine learning models that employ one or more layers of models to generate an output, e.g., a classification, for a received input. Some neural networks include one or more hidden layers in addition to an output layer. The output of each hidden layer is used as input to the next layer in the network, i.e., the next hidden layer or the output layer of the network. Each layer of the network generates an output from a received input in accordance with current values of a respective set of parameters.

SUMMARY

In general, this specification describes a neural network for processing graph data.

In general, one innovative aspect of the subject matter described in this specification can be embodied in methods that include the actions of receiving graph data representing an input graph comprising a plurality of vertices connected by edges; generating, from the graph data, vertex input data representing characteristics of each vertex in the input graph and pair input data representing characteristics of pairs of vertices in the input graph; and generating order-invariant features of the input graph using a neural network, wherein the neural network comprises: a first subnetwork configured to generate a first alternative representation of the vertex input data and a first alternative representation of the pair input data from the vertex input data and the pair input data; and a combining layer configured to receive an input alternative representation and to process the input alternative representation to generate the order-invariant features.

Implementations can include one or more of the following features. Processing the order-invariant features through one or more neural network layers to generate a classification of the graph data. The graph data represents a molecule, and wherein each vertex in the graph is an atomic element in the molecule and each edge is a type of bond between two atomic elements in the molecule. Processing the order-invariant features to determine a likelihood that the molecule represented by the graph data binds to a particular target molecule. The characteristics of each vertex comprise at least one or more of the following: an atomic element represented by the vertex, whether the atomic element represented by the vertex is a hydrogen bond donor or acceptor, a chirality of the atomic element, a formal charge of the atomic element, the hybridization state of the atomic element, or a set of sizes of rings of which this atomic element is a part. The characteristics of each pair of vertices comprise at least one or more of the following: a type of bond between the atomic elements represented by the vertices, or a length of a path between the atomic elements represented by the vertices. The plurality of layers further comprises: one or more other subnetworks that collectively process the first alternative representations to generate a second alternative representation of the pair input data and a second alternative representation of the vertex data and provide the second alternative representations as input to the combining layer. The first subnetwork is configured to, for each vertex in the input graph: apply a first vertex function to the vertex input data for the vertex to generate a first vertex output; apply a second vertex function to the pair input data for each pair that includes the vertex to generate a respective output for each of the pairs; combine the respective outputs for each of the pairs with a commutative function to generate a second vertex output; and generate the first alternative representation of the vertex input data from the first vertex output and the second vertex output. The first subnetwork is configured to, for each pair of vertices in the input graph: apply a first pair function to the pair input data for the pair to generate a first pair output; generate a second pair output from the vertex input data for vertices in the pair; and generate the first alternative representation of the pair input data for the pair from the first pair output and the second pair output. Generating the second pair output comprises: applying a non-commutative function to vertex input data for a first vertex in the pair as a first input to the non-commutative function and for a second vertex in the pair as a second input to the non-commutative function to generate a first non-commutative output; applying the non-commutative function to vertex input data for the second vertex as the first input to the non-commutative function and the first vertex as the second input to the non-commutative function to generate a second non-commutative output; and applying a commutative function to the first non-commutative output and the second non-commutative output to generate the second pair output. Generating, from the graph data, triplet input data representing characteristics for a triplet of vertices in the graph; wherein the first subnetwork of layers is configured to generate a first alternative representation of the triplet input data; and wherein the first subnetwork is further configured to, for each pair of vertices: apply a second pair function to the triplet input data for each triplet where the pair is the first and third element of the triplet to generate a respective output for each of the triplets; combine the respective outputs for each triplet with a commutative function to generate a third pair output; and wherein generating the first alternative representation for the pair input data comprises generating the first alternative representation for the pair input data from the first pair output, the second pair output, and the third pair output. Generating, from the graph data, triplet input data representing characteristics for a triplet of vertices in the graph; wherein the first subnetwork is further configured to, for each triplet of vertices in the input graph: apply a first triplet function to the triplet input data for the triplet to generate a first triplet output; generate a second triplet output from the pair input data for pairs of vertices in the triplet; and generate a first alternative representation of the triplet input data from the first triplet output and the second triplet output. Generating the second triplet output comprises: identifying a first pair of vertices comprising a first vertex and a second vertex in the triplet; identifying a second pair of vertices comprising the first vertex and a third vertex in the triplet; identifying a third pair of vertices comprising the second vertex and the third vertex; applying a non-commutative function to pair input data for the first pair of vertices as a first input to the non-commutative function, for the second pair of vertices as a second input to the non-commutative function, and for the third pair of vertices as a third input to the non-commutative function to generate a first non-commutative output; applying the non-commutative function to pair input data for the third pair of vertices as the first input to the non-commutative function, for the second pair of vertices as the second input to the non-commutative function, and for the first pair of vertices as the third input to the non-commutative function to generate a second non-commutative output; and applying a commutative function to the first non-commutative output and the second non-commutative output to generate the second triplet output.

Particular embodiments of the subject matter described in this specification can be implemented so as to realize one or more of the following advantages. A neural network can generate a classification from input data representing an undirected graph of vertices connected by edges. Generally, converting a graph to data to be processed by a neural network requires the graph to be sequenced in a particular order. Some neural networks can output different classifications for different sequences of the graph even though elements of the graph remain the same. The neural network described in this specification allows graphs of vertices to be sequenced in any order while still having the same neural network output classification. For example, the neural network can receive a graph that represents a molecule and effectively process the graph to generate an output, e.g., a classification that defines a likelihood that the molecule will bind to a particular target molecule. As a consequence of having the output of the network be independent of an ordering of the elements of the graph when represented as an input, the neural network has to learn fewer parameters, which leads to a better performing and simpler to use model.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
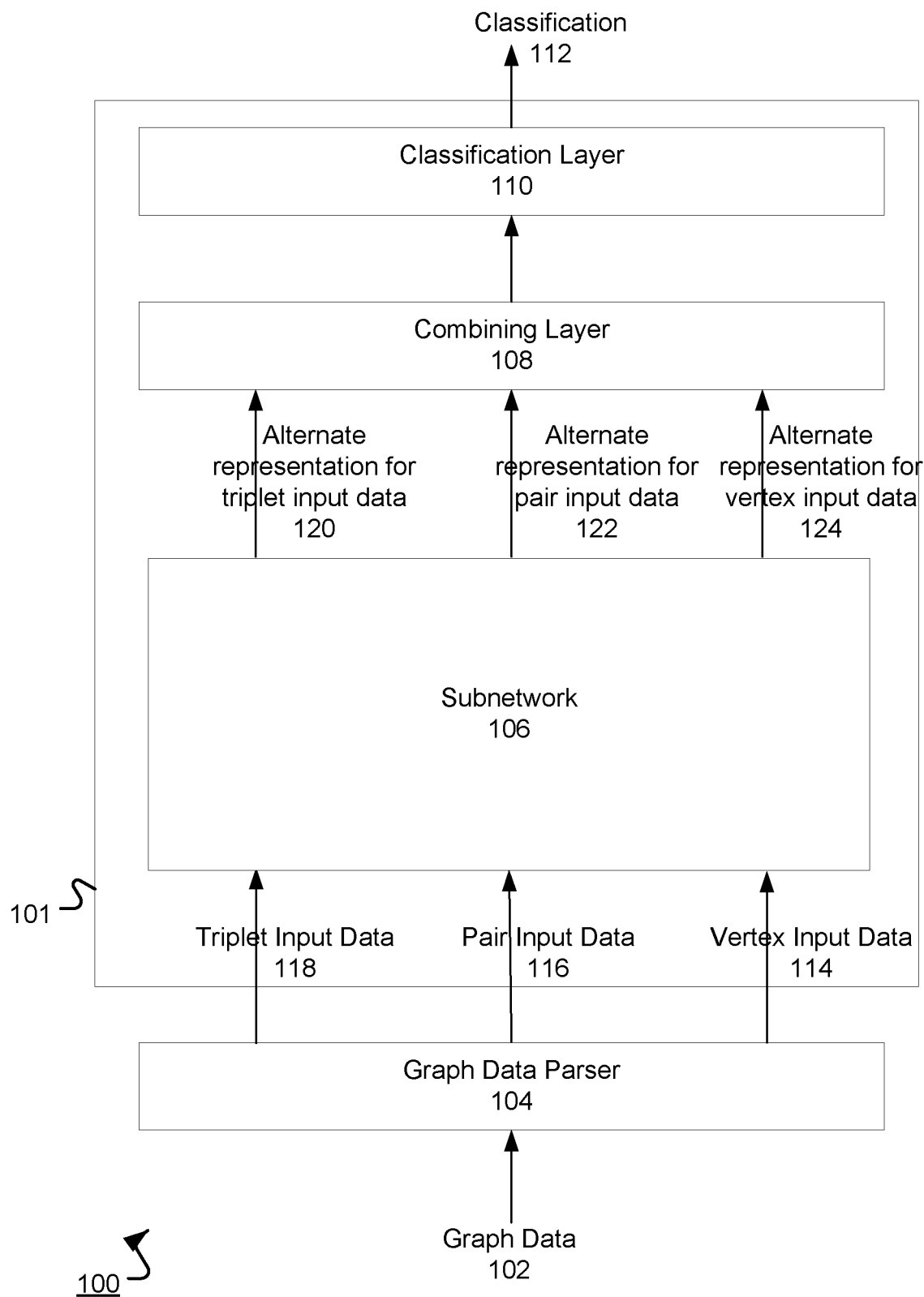
FIG. 1 illustrates an example system for processing graph data.

FIG. 1 illustrates an example system 100 for processing graph data. The system 100 is an example of a system implemented as computer programs on one or more computers in one or more locations, in which the systems, components, and techniques described below can be implemented.

The system 100 includes a neural network 101 and a graph data parser 104. The graph data parser 104 can receive graph data 102 that represents an undirected graph having vertices connected by edges. The graph data parser 104 generates input data for the neural network 101 from the graph data and the neural network 101 processes the input data to generate a classification 112 for the graph.

In some implementations, the graph represents a molecule—the vertices of the graph represent atomic elements in the molecule and the edges represent bonds that connect the atomic elements together. For example, a water molecule ($H2O$) can be represented in graph data as having three vertices and two edges connecting the vertices: H—O—H, and the neural network 101 can process the graph representing the water molecule to generate a score that represents the likelihood that the water molecule binds to a target protein.

The graph data can also include additional data about the vertices and edges. For example, the additional data can specify, for each edge connecting a pair of vertices, a type of bond represented by the edge, e.g., a single bond, a double bond, or a triple bond. The additional data can specify attributes of an atomic element represented by a vertex, which will be described further below with reference to FIG. 2.

The graph data parser 104 generates vertex input data 114, pair input data 116, and, optionally, triplet input data 118 from the graph data 102, all of which will be described with reference to FIG. 2.

A subnetwork 106 in the neural network 101 processes the vertex input data 114, the pair input data 116, and the triplet input data 118 to generate alternate representations of the vertex input data 124, pair input data 122, and triplet input data 120. The subnetwork 106 applies multiple functions to the input data 102-124 to generate the alternative representations so that order-invariance is maintained. Generating the alternative representations using the subnetwork 106 will be described further below with reference to FIGS. 3-8.

In some implementations, instead of having only one subnetwork 106, the neural network 101 also includes one or more other subnetworks. In these implementations, the subnetworks are arranged in a sequence. The subnetworks can collectively process the alternative representations to generate additional alternative representations of the vertex, pair, and triplet input data. That is, each subnetwork after the subnetwork 106 in the sequence processes the alternative representations generated by the preceding subnetwork in the sequence to generate another set of alternative of representations. The last subnetwork in the sequence can provide the alternative representation generated by the subnetwork as an input to a combining layer 108.

The combining layer 108 can process the alternative representations, e.g., the alternative representations 120-124 or the output alternative representation from the last subnetwork, to generate order-invariant features of the graph data 102. In some implementations, if there are multiple subnetworks, the combining layer 108 processes the alternative representation outputs from each subnetwork.

The combining layer 108 can generate the output from moments derived from input alternative representations. The moments can be a measure of a shape of the alternative representations. For example, the first moment of a particular alternative representation can be a mean value, the second moment can be a variance, and the third moment can be a skewness. The combining layer 108 can derive the moments from each input alternative representation. Then, the combining layer 108 can apply a set of parameters to each moment, e.g., compute a dot product of the set of parameters and each moment, to generate an output for the combining layer 108, i.e., the order invariant features of the graph data. The set of parameters can be adjusted during training, which will be described below. In some implementations, the combining layer 108 can generate order invariant features by computing a histogram of values of each dimension in the alternative representations 120-124.

Order-invariant features are features that are the same regardless of what order the graph is sequenced and inputted to the neural network 101. Classifying order-invariant features of the graph can reduce errors during classification. By way of illustration, a molecule can have three atomic elements occupying a multidimensional space: X, Y, and Z. Graph data for the molecule can be sequenced in a first orientation as XYZ, and graph data for the molecule can also be sequenced in a second orientation as ZYX. Some neural networks may generate different features for the differently sequenced molecules because of the order in which the graph is sequenced. However, the neural network 101 would generate the same order-invariant features for the molecule sequenced in the first orientation and the molecule sequenced in the second orientation. Processing graph data, regardless of how it is sequenced, through layers of the neural network 101 as described in this specification enables generation of order-invariant features of the graph data and, therefore, a consistent classification of the graph data sequenced in any way.

The classification layer 110 can then process the output of the combining layer 108 to generate a classification 112 for the graph data 102. For example, the classification layer 110 can apply a respective set of parameters to inputs to the layer to generate the classification 112. In some implementations, instead of generating the classification 112 at one layer, i.e., the classification layer 110, the neural network 101 can generate the classification 112 from the order-invariant features using multiple layers arranged in a sequence. In some implementations, if the graph data 102 represents a molecule, the classification 112 can be a score that represents a likelihood that the molecule represented by the input graph binds to a particular target molecule.

To make the classification, the system 100 can train the neural network 101 using conventional neural network training techniques. For example, the neural network 101 can be trained on training data specifying molecules, and for each molecule, whether the molecule binds to a particular target molecule, e.g., a target protein. The system 100 can adjust parameters used in each layer and subnetwork of the neural network 101 by backpropagating errors. After training, the neural network 101 can classify input graph data input to generate classifications.

Figure 2:
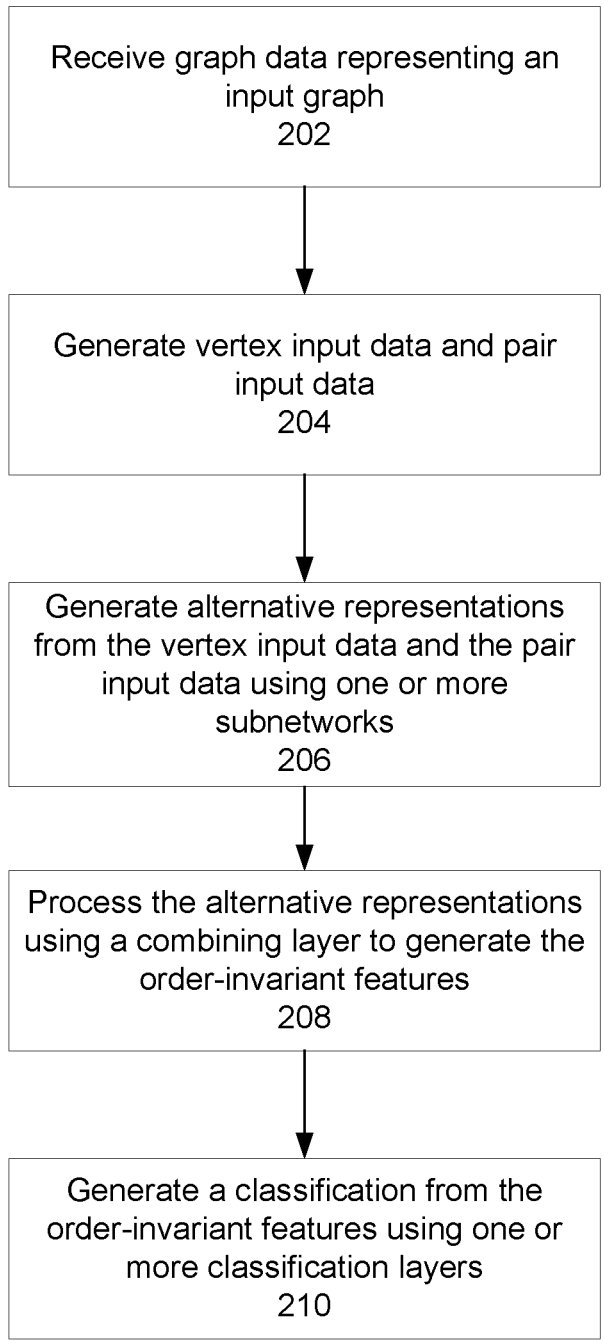
FIG. 2 is a flow diagram of an example method for processing graph data using a neural network.

FIG. 2 is a flow diagram of an example method for processing graph data at a neural network. For convenience, the method 200 will be described with respect to a system, e.g., the system 100 of FIG. 1, having one or more computing devices that execute software to implement the method 200.

The system receives graph data representing an input graph (step 202). The graph includes multiple vertices connected by edges. The graph also corresponds with additional data describing properties of the vertices and the edges. For example, if a graph is of a molecule, the corresponding additional data can specify properties of atomic elements represented by each vertex, properties of bonds between the atomic elements, or other molecular properties.

The system generates vertex input data and pair input data from the graph data (step 204). The vertex input data and the pair input data can be provided to a subnetwork. To generate the vertex input data, the system can identify vertices in the graph. The vertex input data can also include additional data about vertices. For example, in a molecular context, the additional data can include whether the atomic element represented by the vertex is a hydrogen bond donor or acceptor, the chirality of the atomic element, a formal charge of the atomic element, the hybridization state of the atomic element, a set of sizes of rings of which this atomic element is a part, or other atomic element characteristics.

To generate the pair input data, the system can identify pairs of vertices in the graph. Each vertex can be paired with any other vertex in the graph to form a pair. The pair input data can also include additional data about pairs of vertices. For example, the additional data can include a type of bond between the atomic elements represented by the vertices or a length of a path between the atomic elements represented by the vertices. The pair input is unordered. If X and Y are vertices, then the pair input for XY is the same as YX.

In some implementations, the system generates triplet input data from the graph data. Similar to generating vertex input data and pair input data, the system can identify triplets of vertices in the graph. The triplet input data can also include additional data for the triplets of vertices. For example, in a molecular context, the additional data can include a length of a path from a first vertex to a second vertex in the triplet, a length of a path from the second vertex to a third vertex in the triplet, or other molecular characteristics. The triplet input is only partially unordered. The input for XYZ must be the same as ZYX but may be distinct from YXZ.

The vertex input data, pair input data, and triplet input data can each be a vector of numbers representing the input graph. For example, if the input graph represents a molecule, the vertex input data can represent the type of molecule by an atomic number. The pair input data can represent a particular pair of vertices by one or more numbers that map to positions of the pair of vertices in the input graph and a type of bond between the pair of vertices. In some implementations, the pair input data is a vector, and a position in the vector corresponds to a position in the input graph like an adjacency matrix. Similarly, the triplet input data can represent a particular triplet of vertices by one or more numbers that map to positions of the triplet of vertices in the input graph. Other characteristics for the input graph can be mapped to numerical values in similar ways. In some implementations, the characteristics for vertices, pairs of vertices, or triplets of vertices are represented as one-hot vectors. By way of illustration, a bond type of single, double, or triple can be represented as 100, 010, or 001, respectively.

The system generates alternative representations from the vertex input data, the pair input data, and, optionally, the triplet input data by processing the data using one or more subnetworks (step 206). The system applies multiple functions to the vertex, pair, and triplet input data to generate the alternative representations. In all alternate representation, the pair data is unordered and the triple data is partially unordered. If X, Y, and Z are vertices, the alternate pair representations for XY and YX must be identical and the alternate representations for triples XYZ and ZYX must be identical. The multiple functions will be described further below with reference to FIGS. 3-8 and all of them maintain unordered pair data and partially unordered triple data.

The system processes the alternative representations using a combining layer to generate the order-invariant features (step 208). The combining layer can apply a set of trained parameters to the alternative representations to generate the order-invariant features, as described above with reference to FIG. 1.

The system generates a classification of the input graph from the order-invariant features by processing the order-invariant features using the one or more classification layers (step 210). The one or more classification layers can apply a set of trained parameters to the order-invariant features to generate the classification, as described above with reference to FIG. 1.

Figure 3:
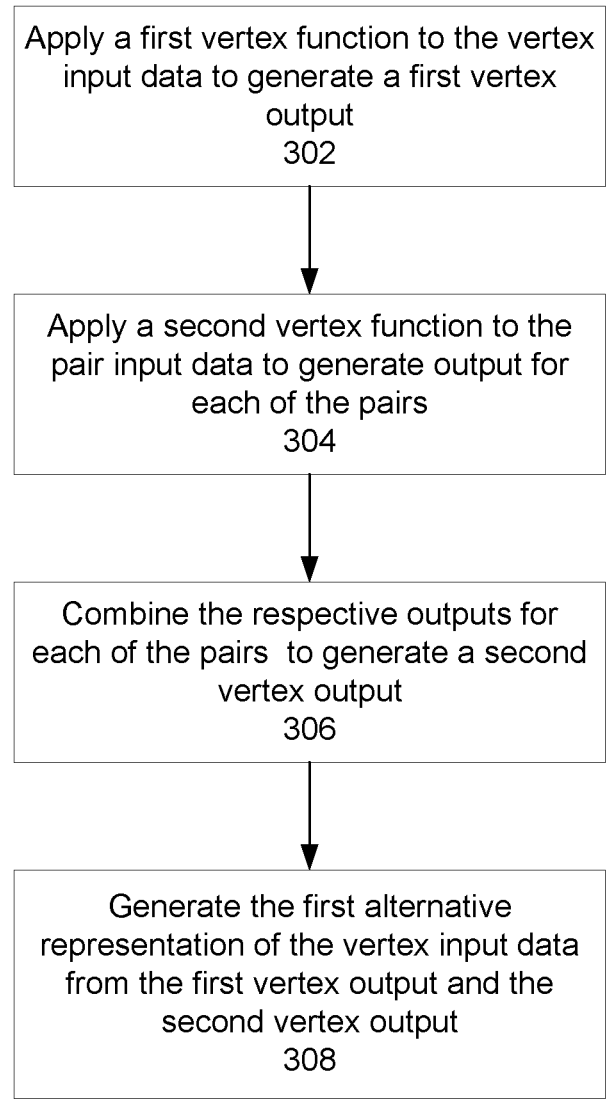
FIG. 3 is a flow diagram of an example method for generating an alternative representation of vertex input data.

FIG. 3 is a flow diagram of an example method 300 for generating an alternative representation of vertex input data using a subnetwork. For convenience, the method 300 will be described with respect to a system, e.g., the system 100 of FIG. 1, having one or more computing devices that execute software to implement the method 300.

The system can perform the following operations 302-308 for each vertex of an input graph to the system to generate the alternative representation of the vertex input data.

For each vertex, the system applies a first vertex function to the vertex input data for the vertex (step 302) to generate a first vertex output. The first vertex function can be a linear or non-linear function. For example, the first vertex function can be an inverse tangent function. The first vertex function can also be Relu (WX+b), where X is the vertex input data as a vector of length n, W is a weight matrix of size m×n, b is a bias vector of length m, and Relu is an element wise non-linearity function, e.g., a rectifier. Parameters of the first vertex function can be adjusted during training.

The system applies a second vertex function to the pair input data for each pair that includes the vertex (304) to generate a respective output for the pair of vertices. In particular, for a given vertex X, the system identifies each pair of vertices in the input graph that includes the vertex X. For each pair, the system applies the second vertex function to the pair input data to generate the output for the pair. By way of illustration, the second vertex function can perform a matrix multiply between a particular parameter matrix and the pair input data for each pair including the vertex. The second vertex function can also apply an element wise non-linearity function on an output of the matrix multiply. Parameters of the second vertex function, e.g., the entries of the parameter matrix can be adjusted during training of the system.

The system combines the outputs for each of the pairs with a commutative function to generate a second vertex output (step 306). The commutative function is a function that returns the same output regardless of the order of the inputs to the function. For example, the system can combine the outputs to generate the second vertex output by computing a sum or average of the outputs.

The system generates the alternative representation of the vertex input data for the vertex from the first vertex output and the second vertex output, e.g., using a commutative or non-commutative function (step 308). For example, the system can sum the first vertex output and the second vertex output or can multiply the first and second vertex outputs by weight parameters which can be learned during training.

Figure 4:
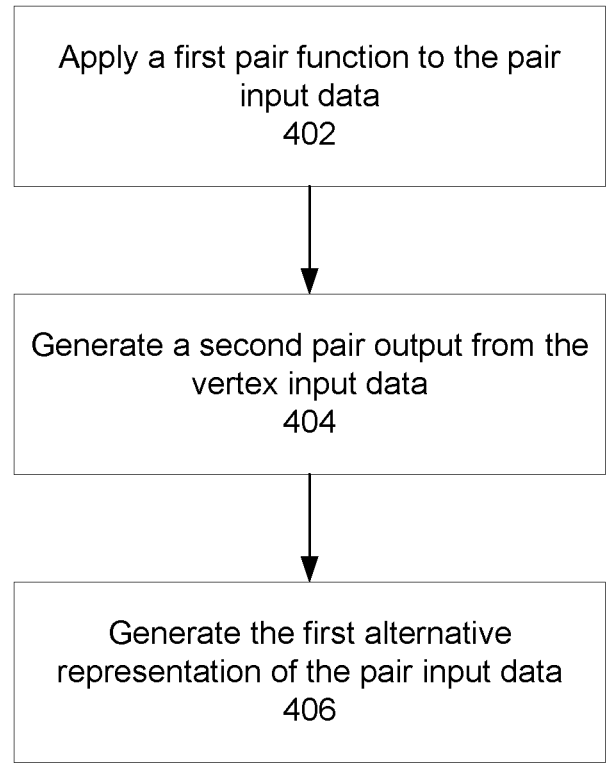
FIG. 4 is a flow diagram of an example method for generating an alternative representation of pair input data.

FIG. 4 is a flow diagram of an example method for generating an alternative representation of pair input data using a subnetwork. For convenience, the method 400 will be described with respect to a system, e.g., the system 100 of FIG. 1, having one or more computing devices that execute software to implement the method 400.

The system can perform the following operations 402-406 for each pair of vertices in an input graph to the system to generate the alternative representation of the pair input data.

For each pair, the system applies a first pair function to the pair input data for the pair (step 402) to generate a first pair output. The first pair function can be a linear or non-linear function. For example, the first pair function can be an inverse tangent function. The first pair function can also be Relu (WX+b), where X is the pair input data as a vector of length n, W is a weight matrix of size m×n, b is a bias vector of length m, and Relu is an element wise non-linearity function, e.g., a rectifier. Parameters of the first pair function can be adjusted during training.

The system generates a second pair output from the vertex input data for vertices in the pair (step 404). For a given pair of vertices (X, Y), the system can identify vertex input data for the vertex X and vertex input data for the vertex Y. The identified vertex input data can be used to generate the second pair output as described further below with reference to FIG. 5.

The system generates the alternative representation of the pair input data for the pair from the first pair output and the second pair output, e.g., using a commutative or non-commutative function (step 406). For example, the system can sum the first pair output and the second pair output or can generate a weighted sum, with the weights being parameters that can be adjusted during training. Optionally, the system also uses a third pair output to generate the alternative representation, which will be described further below with reference to FIG. 6.

Figure 5:
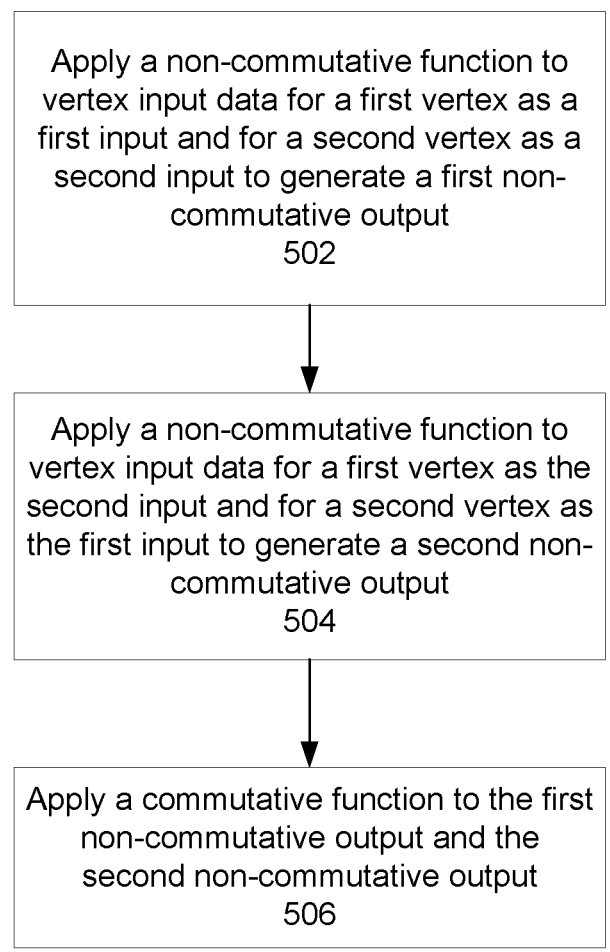
FIG. 5 is a flow diagram of an example method for generating a pair output.

FIG. 5 is a flow diagram of an example method for generating a second pair output using a subnetwork. For convenience, the method 500 will be described with respect to a system, e.g., the system 100 of FIG. 1, having one or more computing devices that execute software to implement the method 500.

For a particular pair of vertices, the system applies a non-commutative function (step 502) to the vertex input data for one vertex in the pair of vertices; and as a second input, vertex input data for a second vertex in the pair of vertices. For example, for a non-commutative function f, the system computes f(X, Y), where X is vertex input data for vertex X and Y is vertex input for vertex Y. As a result, the non-commutative function generates a first non-commutative output. An example of a non-commutative function is y=Relu (W(X,Y)+b), where Relu is a non-linearity function, W is a weight matrix, b is a bias vector, and (X, Y) is a concatenation of input vectors X and Y. y is non-commutative because y (a, b) is not equal to y (b, a).

The system then applies the same non-commutative function (step 504) to the vertex input data for the second vertex as the first input and the vertex input data for the first vertex as the second input to generate a second non-commutative output. That is, in the above example, the system computes f(Y, X).

The system applies a commutative function (step 506) to the first non-commutative output and the second non-commutative output to generate the second pair output of FIG. 4. The commutative function can be a sum function. Parameters for the non-commutative and commutative functions can be adjusted during training.

Figure 6:
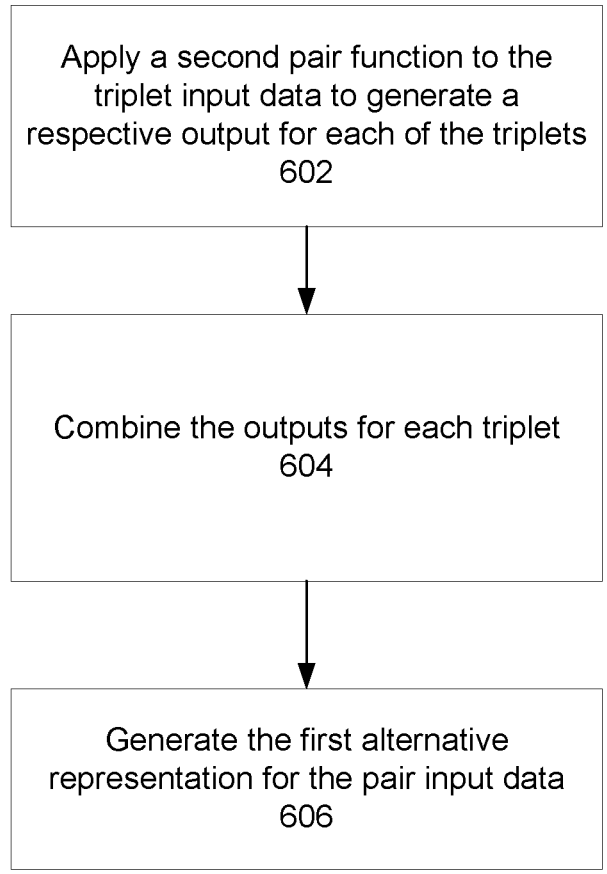
FIG. 6 is a flow diagram of an example method for generating another pair output.

FIG. 6 is a flow diagram of an example method for generating a third pair output using a subnetwork. For convenience, the method 600 will be described with respect to a system, e.g., the system 100 of FIG. 1, having one or more computing devices that execute software to implement the method 600.

For each pair of vertices, the system applies a second pair function to the triplet input data for each triplet that includes the pair of vertices (step 602) as endpoints of the triplet to generate a respective output for the triplet of vertices. That is, given a pair of vertices (X, Y), the system can identify triplet input data for each triplet of vertices in the input graph that has endpoints of X and Y, e.g., (X, A, Y), (X, B, Y), (X, C, Y), and so on. The identified triplet input data can be used as inputs to the second pair function. By way of illustration, the second pair function can perform a matrix multiply between a particular parameter matrix and the triplet input data for each triplet including the pair of vertices. Parameters of the second pair function can be adjusted during training of the system.

The system combines the respective outputs for each of the triplets with a commutative function to generate the third pair output (step 604). For example, the system can combine the outputs to generate the second vertex output by performing a sum or average of the outputs.

The system generates the alternative representation of the pair input data for the pair of vertices from the first pair output of FIG. 4, the second pair output of FIG. 5, and the third pair output, e.g., using a commutative or non-commutative function (step 606). For example, the system can sum the first vertex output and the second vertex output or can generate a weighted sum, with the weights being parameters that can be adjusted during training.

Figure 7:
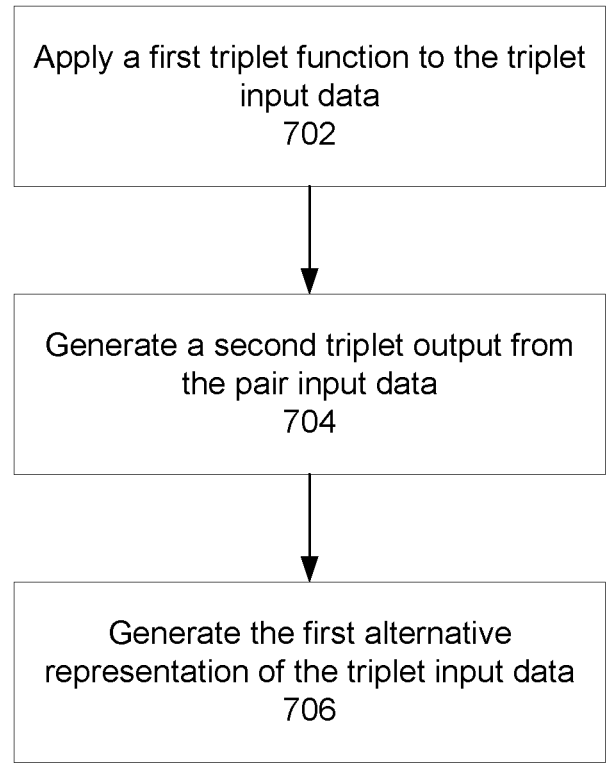
FIG. 7 is a flow diagram of an example method for generating an alternative representation of triplet input data.

FIG. 7 is a flow diagram of an example method for generating an alternative representation of triplet input data using a subnetwork. For convenience, the method 700 will be described with respect to a system, e.g., the system 100 of FIG. 1, having one or more computing devices that execute software to implement the method 700.

The system can perform the following operations 702-706 for each triplet of vertices in an input graph to the system to generate the alternative representation of the triplet input data.

For each triplet, the system applies a first triplet function to the triplet input data for the triplet (step 702) to generate a first triplet output. The first triplet function can be a linear or non-linear function. For example, the first triplet function can be an inverse tangent function. The first triplet function can also be Relu (WX+b), where X is the pair input data as a vector of length n, W is a weight matrix of size m×n, b is a bias vector of length m, and Relu is an element wise non-linearity function, e.g., a rectifier. Parameters of the first triplet function can be adjusted during training, similar to the first vertex function described above with reference to FIG. 3.

The system generates a second triplet output from the pair input data for pairs of vertices in the triplet (step 704). For a given triplet of vertices (X, Y, Z), the system can identify pair input data for the pairs of vertices (X, Y), (X, Z), and (Y, Z). The identified pair input data can be used to generate the second triplet output, which will be described further below with reference to FIG. 8.

The system generates the alternative representation of the triplet input data for the triplet from the first triplet output and the second triplet output, e.g., using a commutative or non-commutative function (step 706). For example, the system can sum the first triplet output and the second triplet output or can generate a weighted sum, with the weights being parameters that can be adjusted during training.

Figure 8:
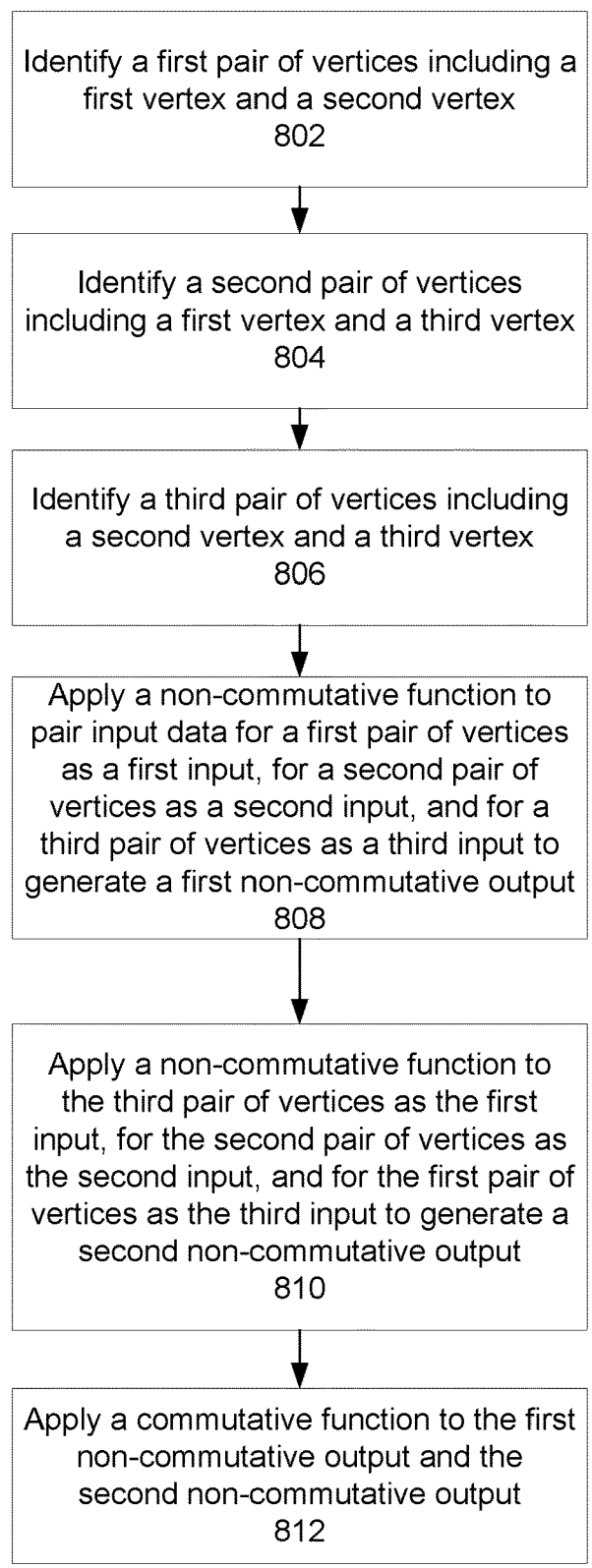
FIG. 8 is a flow diagram of an example method for generating a triplet output.

FIG. 8 is a flow diagram of an example method for generating a second triplet output using a subnetwork. For convenience, the method 800 will be described with respect to a system, e.g., the system 100 of FIG. 1, having one or more computing devices that execute software to implement the method 800.

For a particular triplet of vertices, the system can identify a first pair of vertices including a first vertex and a second vertex in the triplet (step 802), a second pair of vertices including the first vertex and a third vertex in the triplet (step 804), and a third pair of vertices including the second vertex and the third vertex in the triplet (step 806).

The system applies a non-commutative function (step 808) to three inputs: as a first input, pair input data for the first pair of vertices; as a second input, pair input data for the second pair of vertices; and as a third input, pair input data for the third pair of vertices. For example, for a non-commutative function f and triple XYZ, the system computes f([X,Y], [X,Z], [Y,Z]), where [X,Y] is pair input data for the vertices X and Y, [Y, Z] is pair input data for the vertices Y and Z, and [X,Z] is pair input data for the vertices X and Z. As a result, the non-commutative function generates a first non-commutative output. An example of a non-commutative function is Relu (W(X, Y)+b), where Relu is a non-linearity function, W is a weight matrix, b is a bias vector, and Y) is a concatenation of input vectors X and Y.

The system then applies the same non-commutative function (step 810) to the pair input data for the third pair of vertices as the first input, the pair input data for the second pair of vertices as the second input, and the pair input data for the first pair of vertices as the third input. That is, the system computes f([Y,Z], [X,Z], [X,Y]). This causes the non-commutative function to generate a second non-commutative output.

The system applies a commutative function (step 812) to the first non-commutative output and the second non-commutative output to generate the second triplet output of FIG. 7. For example, the commutative function can be a sum function. Parameters for the non-commutative and commutative functions can be adjusted during training.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) monitor, an LCD (liquid crystal display) monitor, or an OLED display, for displaying information to the user, as well as input devices for providing input to the computer, e.g., a keyboard, a mouse, or a presence sensitive display or other surface. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending resources to and receiving resources from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method performed by one or more computers, the method comprising:
   receiving graph data representing an input graph comprising a plurality of vertices connected by edges, wherein the graph data represents a molecule, and wherein each vertex in the graph represents an atomic element in the molecule and each edge represents a bond between two atomic elements in the molecule;
   generating, from the graph data, vertex input data representing characteristics of each vertex in the input graph and pair input data representing characteristics of pairs of vertices in the input graph;
   generating order-invariant features of the input graph using a trained neural network, wherein the trained neural network comprises:
      a first subnetwork configured to generate a first alternative representation of the vertex input data and a first alternative representation of the pair input data from the vertex input data and the pair input data, wherein the first subnetwork is configured to, for each pair of vertices in the input graph:
         apply a first pair function to the pair input data for the pair to generate a first pair output;
         generate a second pair output from the vertex input data for the vertices in the pair, wherein generating the second pair output comprises:
            applying a non-commutative function to the vertex input data for the vertices in the pair with (i) vertex data for a first vertex in the pair as a first input to the non-commutative function and (ii) vertex data for a second vertex in the pair as a second input to the non-commutative function to generate a first non-commutative output, wherein one or more parameters of the non-commutative function have been adjusted during the training of the neural network;
            applying the non-commutative function to the vertex input data for the vertices in the pair with (i) the vertex data for the second vertex in the pair as the first input to the non-commutative function and (ii) the vertex data for the first vertex in the pair as the second input to the non-commutative function to generate a second non-commutative output; and
            applying a commutative function to the first non-commutative output and the second non-commutative output to generate the second pair output; and
         generate the first alternative representation of the pair input data for the pair from at least the first pair output and the second pair output; and
      a combining layer configured to receive at least one input alternative representation and to process the at least one input alternative representation to generate the order-invariant features, wherein the at least one input alternative representation comprises the first alternative representation; and
   processing the order-invariant features through one or more neural network layers to generate a neural network output characterizing the molecule represented by the graph data.

2. The method of claim 1, wherein the neural network output is a classification that represents a likelihood that the molecule represented by the graph data binds to a particular target molecule.

3. The method of claim 1, wherein the characteristics of each vertex comprise at least one or more of the following: an atomic element represented by the vertex, whether the atomic element represented by the vertex is a hydrogen bond donor or acceptor, a chirality of the atomic element, a formal charge of the atomic element, a hybridization state of the atomic element, or a set of sizes of rings of which this atomic element is a part.

4. The method of claim 1, wherein the characteristics of each pair of vertices comprise at least one or more of the following: a type of bond between the atomic elements represented by the vertices, or a length of a path between the atomic elements represented by the vertices.

5. The method of claim 1, wherein the plurality of neural network layers further comprises:
   one or more other subnetworks that collectively process the first alternative representations to generate a second alternative representation of the pair input data and a second alternative representation of the vertex data and provide the second alternative representations as input to the combining layer.

6. The method of claim 1, wherein the first subnetwork is configured to, for each vertex in the input graph:
   apply a first vertex function to the vertex input data for the vertex to generate a first vertex output;
   apply a second vertex function to the pair input data for each pair that includes the vertex to generate a respective output for each of the pairs;
   combine the respective outputs for each of the pairs with a commutative function to generate a second vertex output; and
   generate the first alternative representation of the vertex input data from the first vertex output and the second vertex output.

7. The method of claim 1, further comprising:
   generating, from the graph data, triplet input data representing characteristics for a triplet of vertices in the graph;
   wherein the first subnetwork is configured to generate a first alternative representation of the triplet input data; and
   wherein the first subnetwork is further configured to, for each pair of vertices:
      apply a second pair function to the triplet input data for each triplet where the pair is a first element and a third element of the triplet to generate a respective output for each of the triplets;
      combine the respective outputs for each triplet with a commutative function to generate a third pair output; and
      wherein generating the first alternative representation for the pair input data comprises generating the first alternative representation for the pair input data from the first pair output, the second pair output, and the third pair output.

8. The method of claim 1, further comprising:
generating, from the graph data, triplet input data representing characteristics for a triplet of vertices in the graph;
wherein the first subnetwork is further configured to, for each triplet of vertices in the input graph:
apply a first triplet function to the triplet input data for the triplet to generate a first triplet output;
generate a second triplet output from the pair input data for pairs of vertices in the triplet; and
generate a first alternative representation of the triplet input data from the first triplet output and the second triplet output.

9. The method of claim 8, wherein generating the second triplet output comprises:
identifying a first pair of vertices comprising a first vertex and a second vertex in the triplet;
identifying a second pair of vertices comprising the first vertex and a third vertex in the triplet;
identifying a third pair of vertices comprising the second vertex and the third vertex;
applying a non-commutative function to pair input data for the first pair of vertices as a first input to the non-commutative function, for the second pair of vertices as a second input to the non-commutative function, and for the third pair of vertices as a third input to the non-commutative function to generate a first non-commutative output;
applying the non-commutative function to pair input data for the third pair of vertices as the first input to the non-commutative function, for the second pair of vertices as the second input to the non-commutative function, and for the first pair of vertices as the third input to the non-commutative function to generate a second non-commutative output; and
applying a commutative function to the first non-commutative output and the second non-commutative output to generate the second triplet output.

10. A system comprising:
one or more computers; and
one or more storage devices storing instructions that, when executed by the one or more computers, cause the one or more computers to perform operations comprising:
receiving graph data representing an input graph comprising a plurality of vertices connected by edges, wherein the graph data represents a molecule, and wherein each vertex in the graph represents an atomic element in the molecule and each edge represents a bond between two atomic elements in the molecule;
generating, from the graph data, vertex input data representing characteristics of each vertex in the input graph and pair input data representing characteristics of pairs of vertices in the input graph;
generating order-invariant features of the input graph using a trained neural network, wherein the trained neural network comprises:
a first subnetwork configured to generate a first alternative representation of the vertex input data and a first alternative representation of the pair input data from the vertex input data and the pair input data, wherein the first subnetwork is configured to, for each pair of vertices in the input graph:
apply a first pair function to the pair input data for the pair to generate a first pair output;
generate a second pair output from the vertex input data for the vertices in the pair, wherein generating the second pair output comprises:
applying a non-commutative function to the vertex input data for the vertices in the pair with (i) vertex data for a first vertex in the pair as a first input to the non-commutative function and (ii) vertex data for a second vertex in the pair as a second input to the non-commutative function to generate a first non-commutative output, wherein one or more parameters of the non-commutative function have been adjusted during the training of the neural network;
applying the non-commutative function to the vertex input data for the vertices in the pair with (i) the vertex data for the second vertex in the pair as the first input to the non-commutative function and (ii) the vertex data for the first vertex in the pair as the second input to the non-commutative function to generate a second non-commutative output; and
applying a commutative function to the first non-commutative output and the second non-commutative output to generate the second pair output; and
generate the first alternative representation of the pair input data for the pair from at least the first pair output and the second pair output; and
a combining layer configured to receive at least one input alternative representation and to process the at least one input alternative representation to generate the order-invariant features, wherein the at least one input alternative representation comprises the first alternative representation; and
processing the order-invariant features through one or more neural network layers to generate a neural network output characterizing the molecule represented by the graph data.

11. The system of claim 10, wherein the neural network output is a classification that represents a likelihood that the molecule represented by the graph data binds to a particular target molecule.

12. The system of claim 10, wherein the characteristics of each vertex comprise at least one or more of the following: an atomic element represented by the vertex, whether the atomic element represented by the vertex is a hydrogen bond donor or acceptor, a chirality of the atomic element, a formal charge of the atomic element, a hybridization state of the atomic element, or a set of sizes of rings of which this atomic element is a part.

13. The system of claim 10, wherein the characteristics of each pair of vertices comprise at least one or more of the following: a type of bond between the atomic elements represented by the vertices, or a length of a path between the atomic elements represented by the vertices.

14. The system of claim 10, wherein the plurality of neural network layers further comprises:
one or more other subnetworks that collectively process the first alternative representations to generate a second alternative representation of the pair input data and a second alternative representation of the vertex data and provide the second alternative representations as input to the combining layer.

15. The system of claim 10, wherein the first subnetwork is configured to, for each vertex in the input graph:
apply a first vertex function to the vertex input data for the vertex to generate a first vertex output;

apply a second vertex function to the pair input data for each pair that includes the vertex to generate a respective output for each of the pairs;
combine the respective outputs for each of the pairs with a commutative function to generate a second vertex output; and
generate the first alternative representation of the vertex input data from the first vertex output and the second vertex output.

16. The system of claim 10, the operations further comprising:
generating, from the graph data, triplet input data representing characteristics for a triplet of vertices in the graph;
wherein the first subnetwork is configured to generate a first alternative representation of the triplet input data; and
wherein the first subnetwork is further configured to, for each pair of vertices:
apply a second pair function to the triplet input data for each triplet where the pair is a first element and a third element of the triplet to generate a respective output for each of the triplets;
combine the respective outputs for each triplet with a commutative function to generate a third pair output; and
wherein generating the first alternative representation for the pair input data comprises generating the first alternative representation for the pair input data from the first pair output, the second pair output, and the third pair output.

17. The system of claim 10, the operations further comprising:
generating, from the graph data, triplet input data representing characteristics for a triplet of vertices in the graph;
wherein the first subnetwork is further configured to, for each triplet of vertices in the input graph:
apply a first triplet function to the triplet input data for the triplet to generate a first triplet output;
generate a second triplet output from the pair input data for pairs of vertices in the triplet; and
generate a first alternative representation of the triplet input data from the first triplet output and the second triplet output.

18. The system of claim 17, wherein generating the second triplet output comprises:
identifying a first pair of vertices comprising a first vertex and a second vertex in the triplet;
identifying a second pair of vertices comprising the first vertex and a third vertex in the triplet;
identifying a third pair of vertices comprising the second vertex and the third vertex;
applying a non-commutative function to pair input data for the first pair of vertices as a first input to the non-commutative function, for the second pair of vertices as a second input to the non-commutative function, and for the third pair of vertices as a third input to the non-commutative function to generate a first non-commutative output;
applying the non-commutative function to pair input data for the third pair of vertices as the first input to the non-commutative function, for the second pair of vertices as the second input to the non-commutative function, and for the first pair of vertices as the third input to the non-commutative function to generate a second non-commutative output; and
applying a commutative function to the first non-commutative output and the second non-commutative output to generate the second triplet output.

19. One or more non-transitory computer-readable media having instructions stored thereon, which, when executed by one or more computers, cause the one or more computers to perform operations comprising:
receiving graph data representing an input graph comprising a plurality of vertices connected by edges, wherein the graph data represents a molecule, and wherein each vertex in the graph represents an atomic element in the molecule and each edge represents a bond between two atomic elements in the molecule;
generating, from the graph data, vertex input data representing characteristics of each vertex in the input graph and pair input data representing characteristics of pairs of vertices in the input graph;
generating order-invariant features of the input graph using a trained neural network, wherein the trained neural network comprises:
a first subnetwork configured to generate a first alternative representation of the vertex input data and a first alternative representation of the pair input data from the vertex input data and the pair input data, wherein the first subnetwork is configured to, for each pair of vertices in the input graph:
apply a first pair function to the pair input data for the pair to generate a first pair output;
generate a second pair output from the vertex input data for the vertices in the pair, wherein generating the second pair output comprises:
applying a non-commutative function to the vertex input data for the vertices in the pair with (i) vertex data for a first vertex in the pair as a first input to the non-commutative function and (ii) vertex data for a second vertex in the pair as a second input to the non-commutative function to generate a first non-commutative output, wherein one or more parameters of the non-commutative function have been adjusted during the training of the neural network;
applying the non-commutative function to the vertex input data for the vertices in the pair with (i) the vertex data for the second vertex in the pair as the first input to the non-commutative function and (ii) the vertex data for the first vertex in the pair as the second input to the non-commutative function to generate a second non-commutative output; and
applying a commutative function to the first non-commutative output and the second non-commutative output to generate the second pair output; and
generate the first alternative representation of the pair input data for the pair from at least the first pair output and the second pair output; and
a combining layer configured to receive at least one input alternative representation and to process the at least one input alternative representation to generate the order-invariant features, wherein the at least one input alternative representation comprises the first alternative representation; and
processing the order-invariant features through one or more neural network layers to generate a neural network output characterizing the molecule represented by the graph data.

20. The media of claim 19, wherein the neural network output is a classification that represents a likelihood that the molecule represented by the graph data binds to a particular target molecule.

* * * * *